United States Patent
Hernandez

(10) Patent No.: US 10,709,905 B2
(45) Date of Patent: Jul. 14, 2020

(54) METHOD OF CALCULATING A TONGUE-AND-GROOVE EFFECT OF A MULTI-LEAF COLLIMATOR

(71) Applicant: Victor Hernandez, Tarragona (ES)

(72) Inventor: Victor Hernandez, Tarragona (ES)

(*) Notice: Subject to any disclaimer, the term of this patent is extended or adjusted under 35 U.S.C. 154(b) by 116 days.

(21) Appl. No.: 16/023,861

(22) Filed: Jun. 29, 2018

(65) Prior Publication Data

US 2020/0001117 A1 Jan. 2, 2020

(51) Int. Cl.
*A61N 5/10* (2006.01)
*G21K 1/02* (2006.01)
*G21K 1/04* (2006.01)

(52) U.S. Cl.
CPC .......... *A61N 5/1075* (2013.01); *A61N 5/10* (2013.01); *A61N 5/103* (2013.01); *A61N 5/1036* (2013.01); *A61N 5/1042* (2013.01); *A61N 5/1047* (2013.01); *A61N 5/1048* (2013.01); *A61N 5/1071* (2013.01); *G21K 1/02* (2013.01); *G21K 1/04* (2013.01)

(58) Field of Classification Search
CPC .... A61N 5/103; A61N 5/1036; A61N 5/1042; A61N 5/1045; A61N 5/1047; A61N 5/1048; A61N 5/1071; A61N 5/1075; A61N 5/10; A61B 6/06; A61B 6/58; A61B 6/582; G21K 1/02; G21K 1/04; G21K 1/1043; G21K 1/1046
USPC ................... 378/64, 65, 147, 150–153, 207
See application file for complete search history.

(56) References Cited

U.S. PATENT DOCUMENTS

| | | | | | |
|---|---|---|---|---|---|
| 5,751,781 | A | * | 5/1998 | Brown | A61N 5/01 378/65 |
| 5,847,403 | A | * | 12/1998 | Hughes | A61N 5/1048 250/505.1 |
| 6,560,311 | B1 | * | 5/2003 | Shepard | G06F 19/3481 378/65 |
| 6,618,467 | B1 | * | 9/2003 | Ruchala | A61B 6/032 378/147 |
| 6,661,871 | B2 | * | 12/2003 | Siochi | A61N 5/1031 378/150 |
| 6,795,523 | B2 | * | 9/2004 | Steinberg | A61N 5/1042 378/147 |
| 6,853,705 | B2 | * | 2/2005 | Chang | G21K 1/046 378/65 |
| 6,907,105 | B2 | * | 6/2005 | Otto | A61N 5/1042 378/151 |

(Continued)

OTHER PUBLICATIONS

Hernandez et al., "Commissioning of the tongue-and-groove modelling in treatment planning systems: from static fields to VMAT treatments", Physics in Medicine & Biology, 2017, pp. 6688-6707, vol. 62, No. 16.

(Continued)

*Primary Examiner* — Allen C. Ho
(74) *Attorney, Agent, or Firm* — Young & Thompson

(57) ABSTRACT

Applicant presents an improved manner of modeling and calculating the tongue-and-groove effect in multi-leaf collimators in treatment planning systems and processes. The method is based on subtracting an individualized profile area that is determined for each individual model of MLC. The method also includes how to easily obtain the shape of this non-constant profile based on the tests. The method provides better accuracy, particularly for plans using small MLC gaps.

9 Claims, 19 Drawing Sheets

(56) References Cited

U.S. PATENT DOCUMENTS

| | | | | |
|---|---|---|---|---|
| 7,054,413 B2* | 5/2006 | Steinberg | A61N 5/1042 | 378/147 |
| 7,085,348 B2* | 8/2006 | Kamath | A61N 5/103 | 378/65 |
| 7,095,823 B2* | 8/2006 | Topolnjak | A61N 5/1042 | 378/147 |
| 7,142,635 B2* | 11/2006 | Kamath | A61N 5/1042 | 378/65 |
| 7,257,196 B2* | 8/2007 | Brown | A61N 5/1042 | 378/150 |
| 7,397,902 B2* | 7/2008 | Seeber | G21K 1/046 | 250/505.1 |
| 7,466,797 B2* | 12/2008 | Luan | A61N 5/1042 | 378/65 |
| 7,573,978 B2* | 8/2009 | Kamath | G21K 1/04 | 378/65 |
| 7,609,811 B1 | 10/2009 | Siljamaki et al. | | |
| 7,796,731 B2* | 9/2010 | Nord | G21K 1/046 | 378/149 |
| 7,856,082 B2* | 12/2010 | Flynn | A61N 5/103 | 250/492.1 |
| 7,880,154 B2* | 2/2011 | Otto | A61N 5/103 | 250/505.1 |
| 7,906,770 B2* | 3/2011 | Otto | A61N 5/1031 | 250/492.3 |
| 7,957,507 B2* | 6/2011 | Cadman | A61N 5/1042 | 378/153 |
| 8,139,718 B2* | 3/2012 | Brown | A61N 5/1042 | 250/505.1 |
| 8,160,204 B2* | 4/2012 | Müller | A61N 5/1048 | 378/65 |
| 8,280,003 B2 | 10/2012 | Torsti et al. | | |
| 8,363,784 B2* | 1/2013 | Sobering | A61N 5/1031 | 378/65 |
| 8,637,841 B2* | 1/2014 | Prince | A61N 5/1045 | 250/492.1 |
| 8,824,638 B2* | 9/2014 | Nicholson | A61B 6/06 | 378/150 |
| 8,952,346 B2* | 2/2015 | Dempsey | A61N 5/1045 | 250/267 |
| 8,971,489 B2* | 3/2015 | Ruan | A61N 5/1031 | 378/151 |
| 9,199,093 B2* | 12/2015 | Brusasco | A61N 5/1048 | |
| 9,289,626 B2* | 3/2016 | Kawrakow | A61N 5/1031 | |
| 9,437,339 B2* | 9/2016 | Echner | G21K 1/046 | |
| 9,443,633 B2* | 9/2016 | Orton | G21K 1/046 | |
| 9,675,271 B2* | 6/2017 | Shvartsman | A61B 5/055 | |
| 9,966,160 B2* | 5/2018 | Kawrykow | G21K 1/046 | |
| 2005/0148841 A1 | 7/2005 | Kamath et al. | | |

OTHER PUBLICATIONS

LoSasso et al., "Physical and dosimetric aspects of a multileaf collimation system used in the dynamic mode for implementing intensity modulated radiotherapy", Medical Physics, 1998, pp. 1919-1927, vol. 25, Issue 10.

Rosca et al., "An EPID response calculation algorithm using spatial beam characteristics of primary, head scattered and MLC transmitted radiation", Medical Physics, 2008, pp. 2224-2234, vol. 35, Issue 6, Part 1.

Yao et al., "Determining the optimal dosimetric leaf gap setting for rounded leaf-end multileaf collimator systems by simple test fields", Journal of Applied Clinical Medical Physics, 2015, pp. 65-77, vol. 16, No. 4.

Bhagwat et al., "An oscillating sweeping gap test for VMAT quality assurance", Physics in Medicine and Biology, 2010, pp. 5029-5044, vol. 55, No. 17.

* cited by examiner

METHOD OF CALCULATING A TONGUE-AND-GROOVE EFFECT OF A MULTI-LEAF COLLIMATOR

FIELD OF THE INVENTION

The invention relates to the calculation of doses produced by a radiation emitting device, and more particularly, to a system and method for more effectively delivering radiation treatment to a patient.

STATEMENT REGARDING PRIOR DISCLOSURES BY THE INVENTOR

The inventor made a prior disclosure of portions of the invention in *Physics in medicine and biology* 62 16 (2017): 6688-6707 (Hernandez et al, 2017), which is expressly incorporated herein by reference in full.

BACKGROUND

Intensity-modulated radiation-therapy (IMRT) is a state-of-the-art technique for administering radiation to cancer patients. The goal of a treatment is to deliver a prescribed amount of radiation to the tumor, while limiting the amount absorbed by the surrounding healthy tissues and organs at risk.

The primary delivery tool for IMRT is a linear accelerator that rotates on a gantry around the patient, emitting "modulated" beams of X-rays. This modulation is accomplished by means of a device known as a multi-leaf collimator (MLC) which is attached to the accelerator. The MLC consists of a number of separate elements, the leaves, that can independently move and are placed side-by-side to shape the radiation beam. These adjustable heavy-metal leaves act as a filter, blocking or allowing radiation through in a precise manner controlled by a computer, in order to tailor the beam shape to the shape of the tumor volume while minimizing exposure of the neighboring structures.

Treatment proceeds by rotating the accelerator around the patient and coordinating the leaf movements in the MLC so that the radiation delivered conforms to some desirable dose distribution at each gantry (beam) angle. In addition to knowing the beam angles, one must also know the MLC aperture for all gantry angles, that determine the beam fluence (or intensity) at each point from every gantry angle. These intensity profiles are represented by fluence maps.

Planning an IMRT treatment requires calculation of the doses from radiation beams, which can be determined through fluence maps (each consisting of different beamlet intensities) or directly from the characteristics of the treatment plan (one of the most important being the MLC positions). The longer an MLC leaf is open at a certain position, the higher the fluence at that position and the higher the dose delivered to the tissue along a straight path from that position (plus some surrounding tissue).

Adequate modeling of a multi-leaf collimator (MLC) is essential for accurate dose calculations in intensity-modulated radiation-therapy (IMRT) treatments involving dynamic MLCs. For this reason, modern treatment planning systems incorporate MLC characteristics such as the leaf end curvature, MLC transmission, and the tongue-and-groove effect.

Many MLC devices use leaves with rounded tip ends, which produces increased transmission in the region near the leaf tip (where the leaf height is smaller) and some radiation passes even through completely closed leaves. This is typically modeled considering leaf edges as straight and accounting for the transmission through rounded leaf ends by computing the fluence after shifting the leaf positions a certain leaf offset. Thus, leaves are pulled back so that the gap for all leaf pairs is increased by twice this leaf offset value, which is defined as the dosimetric leaf gap (DLG) parameter. Hence, the fluence for a completely closed pair of leaves is computed as the fluence produced by a gap equal to the DLG parameter.

Transmission through the MLC is defined as a ratio between the doses from an open field and a field with a fully closed MLC. Transmission between leaves (interleaf transmission) is higher than the average transmission due to the thin layer of air between leaves, which reduces the ability of the MLC to shield the beam. Therefore, many MLC models have a "tongue-and-groove" design, where the sides of adjacent leaves interlock in order to minimize interleaf transmission. The tongue-and-groove design is illustrated in FIGS. 1 and 2.

This design reduces interleaf transmission, but it increases the effective leaf width when leaves project out into the beam due to the protruding part of the leaves and, in general, whenever the leaf sides are exposed. The tongue-and-groove effect is modeled by modifying the fluence used to calculate the dose distribution. To this aim the projections of the leaf sides are typically extended a constant width in the direction perpendicular to the leaf motion, which produces a reduction in the resulting fluence map. However, this arrangement can produce underdosage between adjacent leaf pairs in asynchronous MLC movements due to this region being further shielded by the tongue of opposing leaf sides in different phases of treatment delivery. This underdosage is known as the tongue-and-groove effect (TG effect). The tongue-and-groove effect is taken into account both in the actual fluence calculation for MLC apertures (static fields and arc fields) and for IMRT fields. The effect is more significant in IMRT treatments than in static MLC delivery techniques.

An exposed tongue in a field modifies the delivered fluence by blocking some additional radiation. The amount of blocking is proportional to the tongue width w. The tongue-and-groove is modeled in the treatment planning system by extending the leaf projections in the direction perpendicular to the leaf motion with a constant extension parameter. This parameter depends on the MLC model and is user-configurable in some treatment planning systems, while in others is fixed and cannot be modified in the treatment planning system configuration. As a consequence of these effects, the fluence map in the direction of leaf motion is increased by the dosimetric leaf gap (each leaf tip being pulled back DLG/2), while in the perpendicular direction it is reduced by a certain width at each leaf side. This difference between the nominal leaf edges and the fluence map used for dose calculations is shown in FIG. 3.

In general, IMRT plans may involve many highly irregular and small MLC apertures and in volumetric-modulated arc therapy (VMAT) individual leaves may repeatedly extend into the radiation field, giving rise to considerable TG effects. Proper modeling of all MLC characteristics is particularly relevant, therefore, in VMAT treatments. Nevertheless, it is difficult for a treatment planning system to fully consider the effects of the beam delivery system. Some investigators have reported that treatment planning system calculations are able to reproduce patterns of dose dips and peaks for a static test field with maximum TG effect, but it has been recently shown that the modeling of the tongueand-groove modeling in treatments with dynamic MLCs is not accurate enough, especially for high resolution MLCs and for small MLC gaps.

SUMMARY

Adequate modeling of the MLC by treatment planning systems is crucial, but the modeling of the tongue-and-groove is often neglected during treatment planning system commissioning. A set of comprehensive tests can be used to evaluate the ability of treatment planning systems to accurately model the tongue-and-groove effect in (a) static fields, (b) sliding window beams and (c) VMAT arcs. The tests are useful for the commissioning of treatment planning systems and for the validation of major upgrades. Such tests can identify dose differences as high as 10% and 7% between the modeled does and the measured dose. These differences indicate inadequate modeling of the tongue-and-groove effect, which might not be identified without the proposed tests.

In particular, the treatment planning systems tend to underestimate the calculated dose, which may require tuning of other configuration parameters in the treatment planning system (such as the dosimetric leaf gap) in order to maximize the agreement between calculations and measurements in clinical plans. There is a need for better modeling of the tongue-and-groove effect of multi-lead collimators by treatment planning systems. Better modeling would improve the accuracy of treatment planning system calculations, especially for plans using small MLC gaps, such as plans with small target volumes or high complexities. Improved modeling can also reduce the need for tuning parameters in the treatment planning system, facilitating a more comprehensive configuration and commissioning of treatment planning systems.

Applicant presents an improved manner of modeling and calculating the tongue-and-groove effect in multi-leaf collimators in treatment planning systems and processes. The method is based on subtracting an individualized profile area that is determined for each individual model of MLC. The method also includes how to easily obtain the shape of this non-constant profile based on the tests. The method provides better accuracy, particularly for plans using small MLC gaps. Applicant's method focuses on the model and its accuracy and not on the algorithm or computer science. Applicant's method improves the accuracy of treatment planning system calculations, particularly for highly modulated plans or those with small target volumes, which involve small MLC gaps and are especially challenging to calculate. In addition, improved modeling of the MLC would greatly reduce the need for tuning parameters in the treatment planning system, facilitating a more comprehensive configuration and commissioning of treatment planning system.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Method 1, Area Subtraction Model

Figure 1:
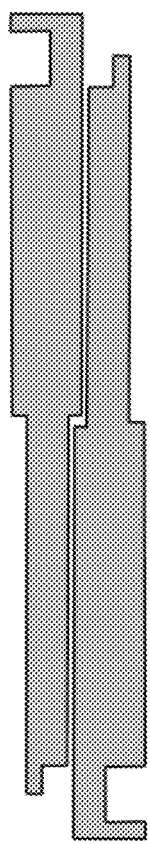
FIG. 1 is a sketch illustrating the tongue-and-groove design of the leaves of a MLC. A frontal section of two adjacent leaves is presented to show the interlock between complementary tongue and groove regions from adjacent leaves.
Figure 2:
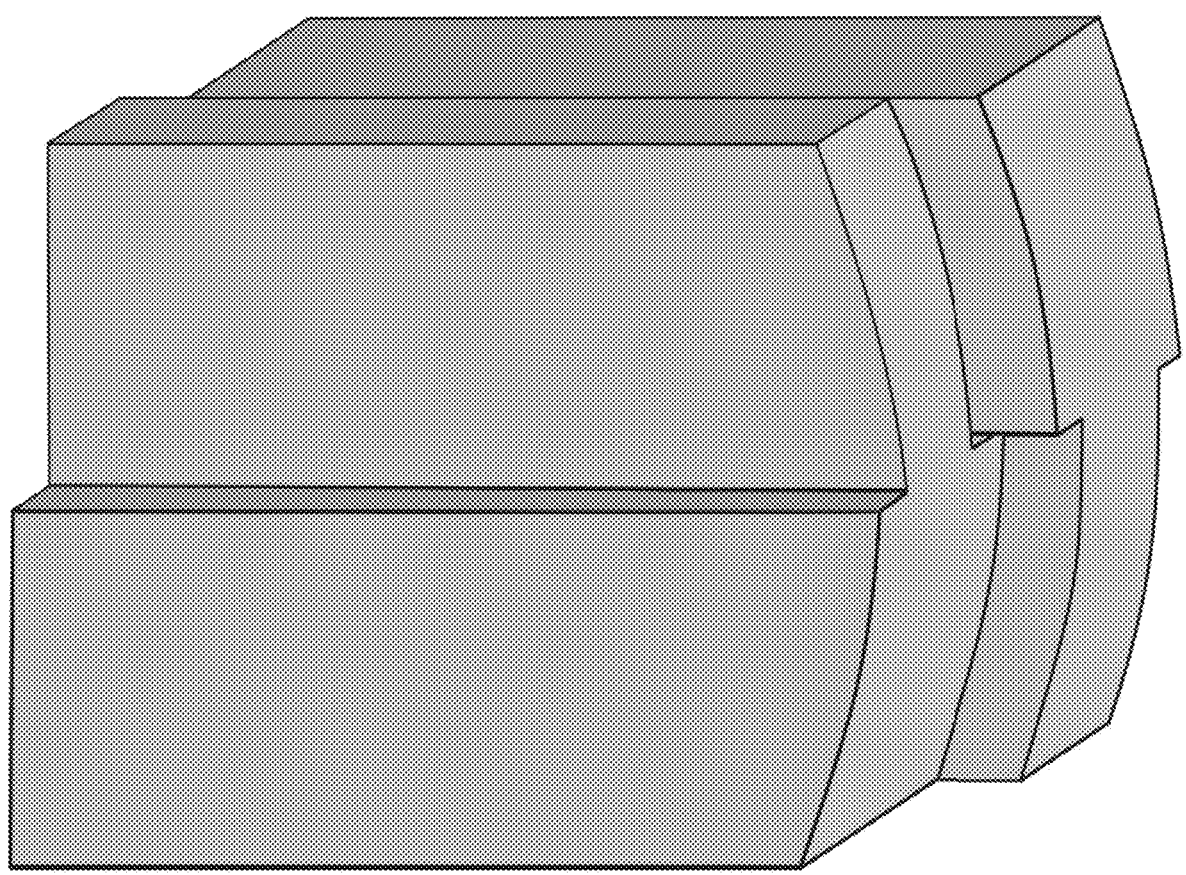
FIG. 2 depicts a 3D view with two adjacent leaves to show both the rounded leaf end and the tongue-and-groove design.
Figure 3:
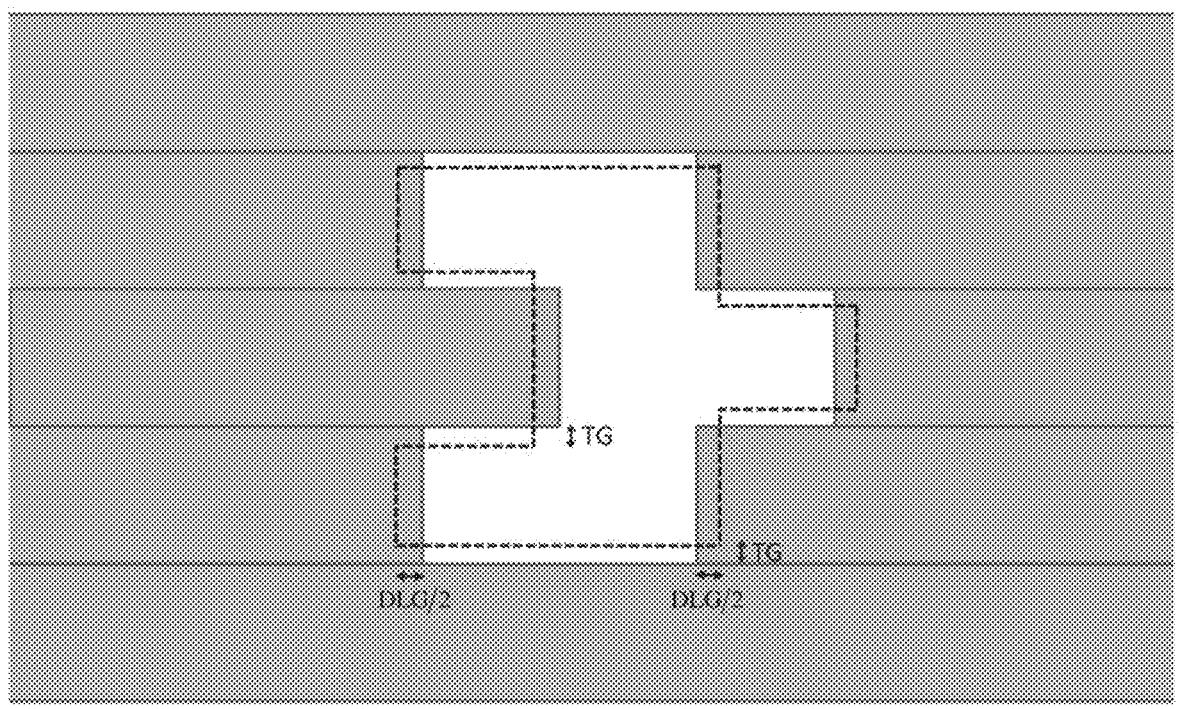
FIG. 3 is a sketch showing leaf positions (in light grey) and the corresponding fluence map used for dose calculations (dashed line) after taking into account the dosimetric leaf gap (DLG) and the tongue-and-groove (TG) effect.

A new method is presented that provides an accurate modeling of the tongue-and-groove (TG). A non-constant width to be subtracted from the fluence at the lateral edges of the leaves that are exposed in the radiation field is assumed. Thus, the total delivered fluence will be reduced and the reduction at each pixel will depend on the position of the pixel and its distance to the leaf end tip. The method provides (1) the experimental tests, (2) the equations, and (3) the methodology to obtain the optimal shape of this non-constant width by direct comparison with measurements. To that aim, simplified theoretical expressions are deduced to calculate the optimal shape of this profile based on experimental measurements.

Theoretical Concepts of Method 1

Consider a dose $D_{SG}$ produced by a generic sweeping MLC gap with a constant gap size. $D_{SG}$ depends on the exposed area of the leaf pair ($A_{leaf\,pair}$) and the MLC transmission and can be expressed as $$D_{SG} = D_{open} \cdot T_{eff} \cdot k \cdot A_{leaf\,pair}, \quad (1)$$

where $D_{open}$ is the dose delivered by the open field (i.e., with the same jaw settings and without MLC) and $T_{eff}$ is the effective MLC transmission. $T_{eff}$ is defined as a function of the mean MLC transmission $T_{mean}$ and the distance d travelled by the MLC leaves as $$T_{eff} = T_{mean} \cdot (d - \text{Gap})/d. \quad (2)$$

In the sweeping gap fields without TG (SGTG0) used to measure the DLG parameter. LoSasso, T., C. S. Chui, and C. C. Ling. (1998). "Physical and dosimetric aspects of a multileaf collimation system used in the dynamic mode for implementing intensity modulated radiotherapy." Med Phys 25(10):1919-1927 (LoSasso et al. 1998).

$$A_{leaf\,pair} = w_{leaf} \cdot \text{Gap}_{eff} \quad (3)$$

where $w_{leaf}$ is the leaf width and the effective gap is defined as $$\text{Gap}_{eff} = \text{Gap} + DLG \quad (4)$$

and Eq. (1) results into $$D_{SGTG0} = D_{open} \cdot T_{eff} + k \cdot w_{leaf} \cdot \text{Gap}_{eff}. \quad (5)$$

Since $w_{leaf}$ is constant, it can be absorbed into a new constant $k_2 = k \cdot w_{leaf}$ and the typical expression is obtained where the quantity $D = D_{SGTG0} - D_{open} \cdot T_{eff}$ can be plotted as a function of the gap and the parameter DLG is derived as the negative gap necessary to produce a quantity D equal to zero (LoSasso et al. 1998).

In clinical cases, however, adjacent leaves differ in their positions and the dose produced by the sweeping gap is affected by the TG effect. To study that problem consider asynchronous sweeping gaps, where there is a difference in the positions of adjacent leaves, thus incorporating TG effects.

Figure 4:
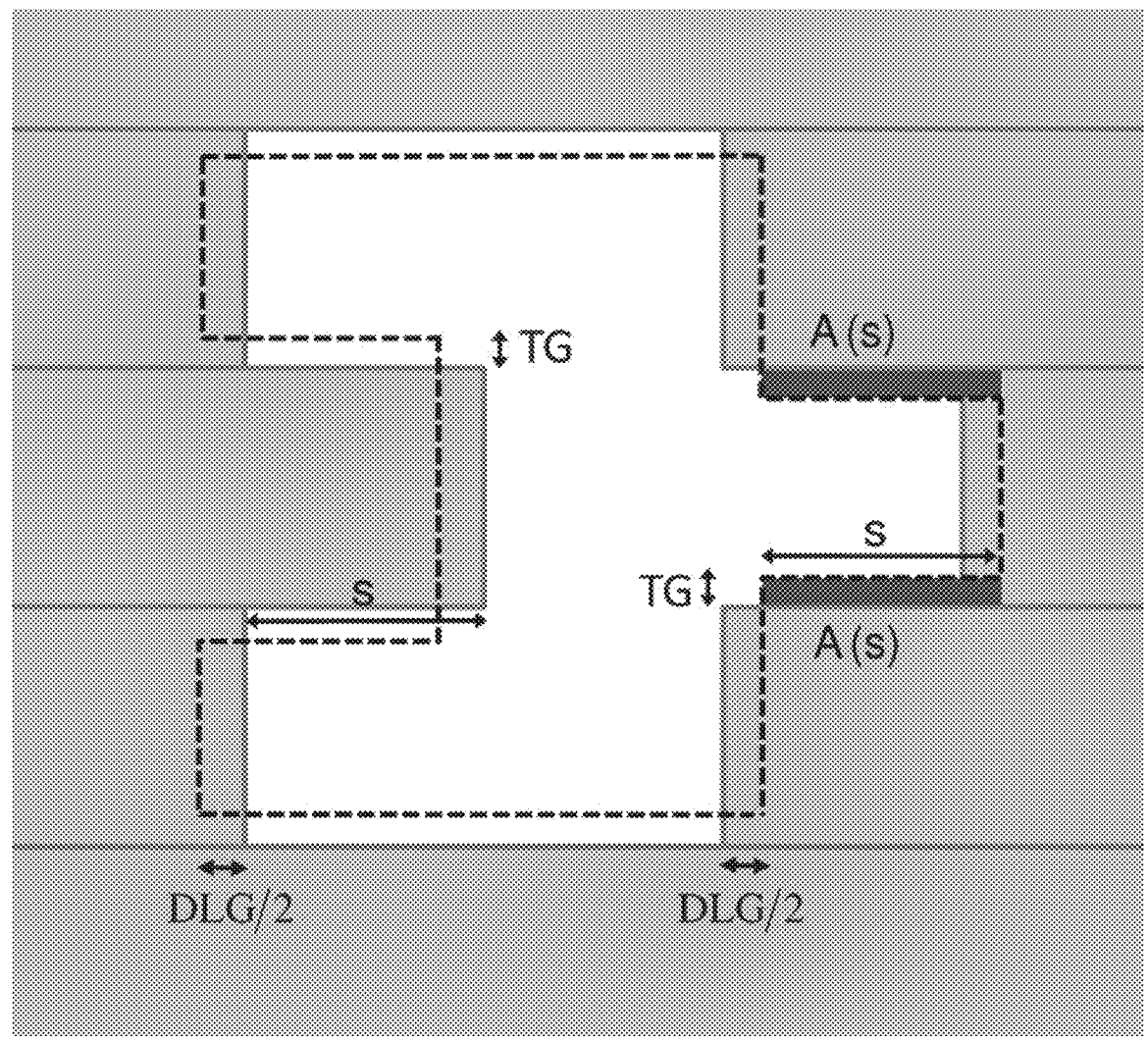
FIG. 4 is a sketch showing leaf positions (in light grey) and the corresponding fluence map used for dose calculations (dashed line) after taking into account the dosimetric leaf gap (DLG) and the tongue-and-groove (TG) effect. The area subtracted to model the TG effect for adjacent leaves with a difference in their position equal to s is represented by A(s) and marked in dark grey.

To account for the TG effect, a certain area $A(s)$ can be subtracted from the fluence map at the exposed leaf sides. $A(s)$ depends on the difference between adjacent leaf positions s and is shown in FIG. 4 (see rectangle in dark grey). The exposed area of the leaf pair for this aSG fields can be expressed as $$A_{leaf\,pair} = w_{leaf} \cdot \text{Gap}_{eff} - 2A(s) \quad (6)$$

and Eq. (1) results into $$D_{aSG}(s) = D_{open} \cdot T_{eff} \cdot k \cdot (w_{leaf} \cdot \text{Gap}_{eff} - 2A(s)) \quad (7)$$

which isolating k from Eq. (5) yields $$D_{aSG}(s) = D_{SGTG0} - 2\frac{D_{SGTG0} - D_{open} \cdot T_{eff}}{w_{leaf} \cdot \text{Gap}_{eff}} A(s). \quad (8)$$

$A(s)$ can then be obtained as $$A(s) = \frac{D_{SGTG0} - D_{aSG}(s)}{D_{SGTG0} - D_{open} \cdot T_{eff}} \left(\frac{\text{Gap}_{eff} \cdot w_{leaf}}{2}\right), \quad (9)$$

that is equivalent to $$A(s) = \frac{D_{SGTG0} - D_{aSG}(s)}{D_{SGTG0} - D_{open} \cdot T\left(\frac{d - \text{Gap}}{d}\right)} \left(\frac{(\text{Gap} + DLG) \cdot w_{leaf}}{2}\right). \quad (10)$$

Experimental Determination of the A(s) Curve

In this section the methodology for the experimental determination of the A(s) curve is presented. Firstly, the asynchronous sweeping gap (aSG) tests and the asynchronous oscillating sweeping gap (aOSG) tests are described. Secondly, the experimental design of the experiments to obtain the average doses needed for computing the A(s) curve with Eq. (10) is provided.

The aSG tests consist of beams that use the sliding window technique, which is characterized by using a static gantry angle and a dynamic MLC pattern where the MLC leaves start at one side of the field and move unidirectionally towards the opposite side while the beam is on. A typical test involving dynamic MLCs is the sweeping gap or sliding slit test (LoSasso et al, 1998). In the sweeping gap test all the leaves are uniformly extended defining a certain gap and move at the same constant speed from one side of the beam to the other. However, since the sweeping gap test involves uniformly extended leaves, it does not generate any TG effect. The aSG tests, on the other hand, are defined with a shift in the position of adjacent leaves. Despite the shift, all leaves move at the same constant speed, keeping the MLC pattern unchanged. The same gap size was produced by all leaf pairs, but, since leaves are not uniformly extended, this test incorporates a certain degree of TG effect that is very well-defined and depends on the value of the shift. A more detailed description of this test can be found in the previous publication Hernández, Víctor, Juan Antonio Vera-Sanchez, Laure Vieillevigne and Jordi Saez. "Commissioning of the tongue-and-groove modelling in treatment planning systems: from static fields to VMAT treatments." *Physics in medicine and biology* 62 (2017): 6688-6707 (Hernandez et al, 2017). Similar tests have been used for other purposes by other investigators. Rosca, Florin & Zygmanski, Piotr. (2008). An EPID response calculation algorithm using spatial beam characteristics of primary, head scattered and MLC transmitted radiation. Medical physics. 35. 2224-34 (Rosca and Zygmanski 2008); Yao W, Farr JB. Determining the optimal dosimetric leaf gap setting for rounded leaf-end multileaf collimator systems by simple test fields. J Appl Clin Med Phys 2015; 16:65-77 (Yao and Farr 2015). Rosca and Zygmanski used them to add corrections to the EPID response prediction algorithm, while Yao and Farr used them to determine the optimal dosimetric leaf gap parameter to be entered into the treatment planning system configuration.

The aOSG tests consist of VMAT arcs where the MLC repeatedly moves across the field at a constant speed during a full gantry rotation. This test is based on the oscillating sweeping gap (OSG) test presented by Bhagwat et al. 2010, but in the OSG test the leaves are uniformly extended and as a consequence it does not originate any TG effect. Similarly to the aSG tests, the aOSG test incorporate TG effects by introducing a shift between the positions of adjacent leaf pairs. Thus, a well-defined amount of TG is defined in each test and this amount depends on the positioning shift applied.

The dose distribution produced by the aSG tests is not flat due both to interleaf transmission and to TG effects (Hernandez et al. 2017). Therefore measurements must be designed to assess the average dose. The aSG tests require only irradiation with a fixed gantry angle. Therefore, they can be performed at gantry zero (in its vertical top position) and a water phantom can be used. A large ion chamber (such as a 0.6 cm$^3$ Farmer-type ion chamber) positioned horizontally, i.e., with its axis perpendicular to the leaf motion direction should preferably be used in order to average the effect of multiple leaves. A(s) should, in principle, be independent of the depth in water used for measurements and of the source-to-surface distance (SSD), therefore typical clinical conditions such as SSD=90 cm and 10 cm depth can be used.

For the aOSG tests a cylindrical phantom should ideally be used, but we showed that other phantoms (for instance cubic) also produced good results (Hernandez et al. 2017). The dose distribution corresponding to the aOSG tests are much more homogeneous because in these tests the interleaf transmission and TG effects are smoothed out during the gantry rotation. However, there is a residual granularity in the dose distribution that also makes it preferable to use a large ion chamber that will average the dose in its active volume. In our previous work (Hernandez et al., 2017) a lateral shift of for instance 5 mm in either the position of the ion chamber or of the whole phantom was recommended in order avoid measuring exactly at the isocenter.

Both tests can be used because they all have a well-defined T&G contribution that can be associated to a specific s value. Once the doses $D_{aSG}$ are measured, A(s) can be calculated using Eq. (10). Thus, if the dose for the aSG tests $D_{aSG}$ is measured for a series of s values, the curve A(s) can be obtained.

Determination of the Optimal Shape of the TG Width and Fluence Computation

For s values smaller than the leaf gap there is no interdigitation between leaves from opposed MLC banks and A(s) is equal to the area of the optimal TG profile from zero to s. However, the area A(s) was defined to be 'subtracted' from the fluence map and some fluence should be assigned to that region to account for MLC transmission through the TG profile. If a transmission value $T_{TG}$ is assigned to the TG profile the previous method and equations are still valid, but the area of the TG profile must be increased by a factor $1/(1-T_{TG})$ in order to produce the same effective reduction. Hence, the area of the TG profile can be expressed as:

$$A_{TG}(s) = \frac{A(s)}{1 - T_{TG}} \tag{11}$$

The optimal shape of the TG width can then be obtained as the first derivative of $A_{TG}(s)$:

$$w_{TG}(s) = \frac{d(A_{TG}(s))}{ds} = \frac{1}{1 - T_{TG}} \frac{d(A(s))}{ds} \tag{12}$$

And the optimal shape of the area to be subtracted (which is equivalent to $w_{TG}$ without considering the transmission through the TG) is equal to:

$$w(s) = \frac{d(A(s))}{ds} \tag{13}$$

Figure 5:
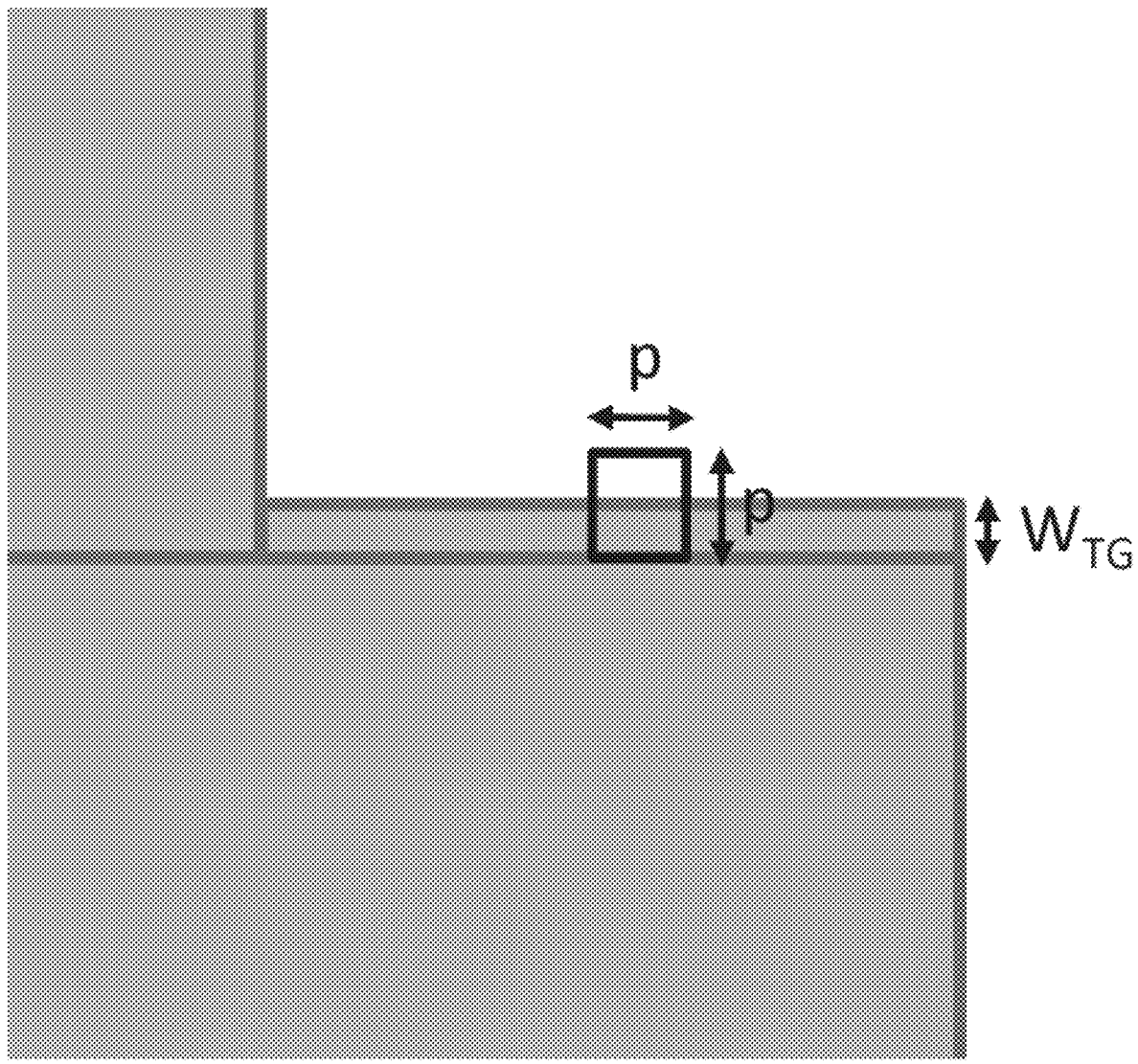
FIG. 5 is a sketch showing the tongue width $w_{TG}$ and a pixel (of pixel size p) including this region.

Let's now consider a pixel located at the lateral edge of a leaf encompassing the TG width $w_{TG}$ (see sketch in FIG. 5). The fluence in the pixel can be expressed as the sum of the direct fluence and the fluence due to the transmission through the tongue:

$$\varphi = \varphi_d + \varphi_T \tag{14}$$

The direct fluence $\varphi_d$ accounts for the fluence delivered in the non-shielded fraction of the pixel. Assuming (for simplicity) a pixel size p greater than $w_{TG}$, $\varphi_d$ can be expressed as:

$$\varphi_d = \frac{p(p - w_{TG}(s))}{p^2} = 1 - \frac{w_{TG}(s)}{p}. \tag{15}$$

And the fluence due to the transmission $T_{TG}$ through the fraction of the pixel shielded by the width $w_T$ can be obtained as:

$$\varphi_T = \frac{p w_{TG}(s)}{p^2} T_{TG} = \frac{w_{TG}(s)}{p} T_{TG}. \tag{16}$$

The total fluence results into:

$$\varphi = \varphi_d + \varphi_T = 1 - \frac{w_{TG}(s)}{p} + \frac{w_{TG}(s)}{p} T_{TG} = 1 - \frac{w_{TG}(s)}{p}(1 - T_{TG}) \tag{17}$$

As expected, when there is no TG width ($w_{TD}$=0) the fluence is equal to 1, while when the pixel size is equal to the TG width (p=$w_{TG}$) the fluence is equal to the TG transmission $T_{TG}$. Substituting the width w(s) obtained in Eq. (12) into Eq. (17) it can be deduced that, for p>$w_{TG}$, $$\varphi = 1 - \frac{(1 - T_{TG})}{p}\left(\frac{1}{1 - T_{TG}}\right)\frac{d(A(s))}{ds} = 1 - \frac{1}{p}\frac{d(A(s))}{ds}, \tag{18}$$

which shows that the fluence can be obtained directly from the experimentally area A(s), without needing the value of $T_{TG}$.

Method 2, Tongue-and-Groove Transmission Model

In this model the geometry of the leaves with a realistic TG geometry is considered and the fluence through the TG width is calculated based on this geometry and physical principles. The results obtain with this model will depend on certain parameters, and these parameters will be derived by comparison with measurements.

In the typical design of the leaves that form the MLC the leaf width is constant and the height of the protruding part of the leave (tongue) is approximately equal to half the total leaf height. However, it is important that for leaves with rounded leaf ends, the height of both the leaf and its tongue are reduced near the leaf tip end due to the leaf end curvature.

Figure 6:
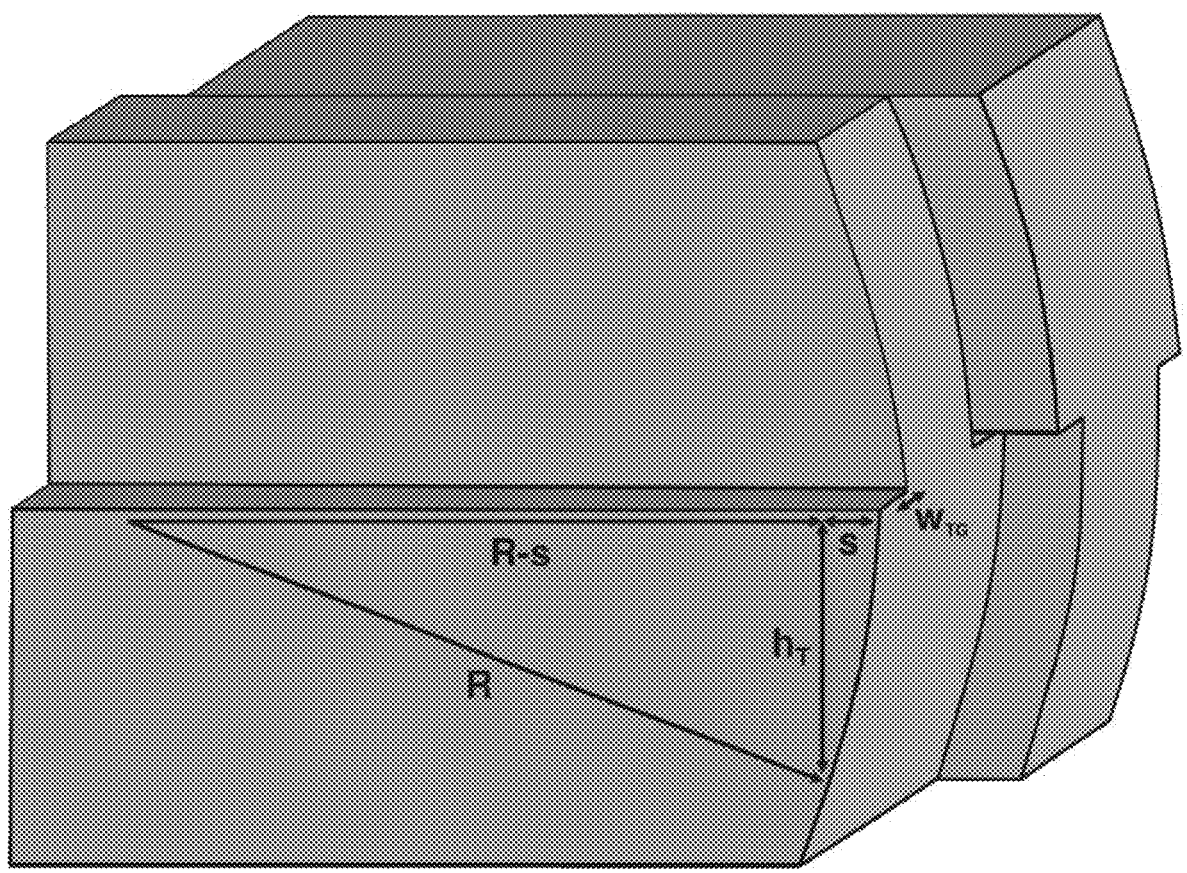
FIG. 6 is a sketch showing the rounded leaf end (with radius R) and the protruding part of the leaf (tongue). The height of the tongue $h_T$ corresponding to a position at a distance s from the leaf tip is also illustrated.

Let's consider an MLC with rounded leaf ends and study the rounded part of the leaf with a curvature of radius R. This geometry is illustrated in the sketch provided in FIG. 6. The height of the tongue $h_T$ at a given distance s from the leaf tip end can be calculated as a function of s as:

$$R^2 = (R-s)^2 + h_T^2 \tag{19}$$

$$h_T = \sqrt{R^2 - (R-s)^2} = \sqrt{2Rs - s^2} = \sqrt{2Rs\left(1 - \frac{s}{2R}\right)}. \tag{20}$$

For the Varian's HD120 MLC, for instance, the leaf curvature radius is R=160 mm and the leaf height is 67.5 mm. Thus, the height of the tongue progressively increases according to Eq. (20) from $h_T$=0 (for s=0) to a maximum value of $h_T$=33.75 mm (half the leaf height), which is reached when s is equal to 3.6 mm. This is a simplified geometry, because there is a transition zone between these two regions, but it allows for a clear description of the method used. In that case $h_T$ can be expressed as:

$$h_T = \begin{cases} \sqrt{2Rs\left(1 - \frac{s}{2R}\right)} & \text{for } s \leq 3.6 \text{ mm} \\ 33.75 \text{ mm} & \text{for } s > 3.6 \text{ mm} \end{cases} \tag{21}$$

As a first approximation, the transmission through the variable tongue height can be calculated assuming an exponential attenuation through the tongue height $h_T$. Thus, the transmission can be expressed as a function of s as:

$$T_{TG}(s) = e^{-\mu h_T} = \begin{cases} e^{-\mu\sqrt{2Rs\left(1-\frac{s}{2R}\right)}} & \text{for } s \leq 3.6 \text{ mm} \\ e^{-\mu 33.75} & \text{for } s > 3.6 \text{ mm} \end{cases} \tag{22}$$

Let's consider a pixel with pixel size p located beneath the tongue width $w_{TG}$ (illustrated in FIG. 5). The fluence in the pixel can be expressed as the sum of (i) the direct fluence and (ii) the fluence due to the transmission through the tongue:

$$\varphi = \varphi_d + \varphi_T \tag{23}$$

The Eq. (17) obtained in method 1 also applies, but in this case it can be expressed as:

$$\varphi = \varphi_d + \varphi_T = 1 - \frac{w_{TG}}{p}(1 - T_{TG}(s)), \tag{24}$$

because in method 1 a non-constant TG width $w_{TG}(s)$ and a constant TG transmission $T_{TG}$ was assumed, while in method 2 a constant TG width $w_{TG}$ and a non-constant transmission $T_{TG}(s)$ is being considered.

As a consequence, if $w_{TG}$ and $T_{TG}(s)$ are known the fluence can be computed. These parameters depend on the design of the leaves ($w_{TG}$, geometry and R) as well as on the attenuation coefficient $\mu$ (which depends on the MLC material and the quality of the radiation beam). If all these parameters are known the resulting fluence can be obtained with simple expressions like the ones used to obtain Eq. (22) or more accurate methods, either analytic or Monte Carlo simulations.

The values of the involved parameters can be adjusted to reproduce the results from the aSG or aOSG tests or to reproduce the experimental A(s) curve (obtained with method 1). Thus, from Eq. (18) and Eq. (24) we can derive that:

$$T_{TG}(s) = 1 - \frac{1}{w_{TG}}\frac{d(A(s))}{ds} \tag{25}$$

Therefore, T(s) can be directly obtained from the experimental A(s) curve. Alternatively, the function A(s) can be obtained as:

$$\frac{d(A(s))}{ds} = w_{TG}(1 - T_{TG}(s)), \tag{26}$$

which yields:

$$A(s) = \int_0^s w_{TG}(1 - T_{TG}(s'))ds'. \tag{27}$$

This integral can be analytically solved very easily if the term $$s\left(1 - \frac{s}{2R}\right)$$

in Eq. (12) is approximated to s, which is a valid approximation for s<3.6 mm because 2R=320 mm. In that case:

$$T_{TG}(s) = e^{-\mu h_T} \approx \begin{cases} e^{-\mu\sqrt{2Rs}} & \text{for } s \leq 3.55 \text{ mm} \\ e^{-\mu 33.75} & \text{for } s > 3.55 \text{ mm} \end{cases} \tag{28}$$

$$A(s) = \begin{cases} \int_0^s w_{TG}(1 - e^{-\mu\sqrt{2Rs'}})ds' & \text{for } s \leq 3.55 \text{ mm} \\ \int_0^{3.55} w_{TG}(1 - e^{-\mu\sqrt{2Rs'}})ds' + \\ \quad \int_{3.55}^s w_{TG}(1 - e^{-\mu 33.75})ds' & \text{for } s > 3.55 \text{ mm} \end{cases} \tag{29}$$

For s≤3.55, A(s) results into:

$$A(s) = w_{TG}\left[s + \frac{\mu\sqrt{2Rs}+1}{\mu^2 R}e^{-\mu\sqrt{2Rs}} - \frac{1}{\mu^2 R}\right] \tag{30}$$

And for s>3.55:

$$A(s)=A(3.55)+w_{TG}(s-3.55) \qquad (31)$$

Comparison of Method 1 and Method 2
To summarize, in Method 1:
A constant TG transmission was considered
A non-constant TG width $w_{TG}(s)$ was assumed or a non-constant width $w(s)$ was subtracted from the fluence map.
Expressions were provided to experimentally obtain the $A(s)$ curves.
The non-constant width $w(s)$ was determined from the $A(s)$ curves.
Fluence and dose calculations can then be accurately performed taking into account the TG effect of the leaves.
While in Method 2:
A physical model based on a realistic geometry of the leaves was considered, with a constant TG width $w_{TG}$ and a non-constant TG transmission $T_{TG}(s)$.
The values of the parameters involved in the model were determined with the experimental results from (i) the aSG, (ii) the aOSG tests or (iii) with the $A(s)$ curves.
Fluence and dose calculations can be accurately performed taking into account the TG effect of the leaves.

Method 1 follows a more empirical approach based on experimental results. Method 2, on the other hand, allows to use a certain physical model and provides a method to determine the parameters involved in the model based on experiments. Both methods are equivalent and produce very similar results. Differences between the two methods are only due to the differences in the fitting function used. For instance, if the function defined by Eq. (29) was used in Method 1 to fit the experimental $A(s)$ curve, the two methods would be coincident and would produce exactly the same expressions. Other physical models can be used in method 2, but they will all produce similar (and accurate) results as long as they reproduce the experimental $A(s)$ curve.

EXAMPLES

It should be understood that the examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof.

In this section several examples of the described methods are presented. In example 1 the methods are applied to two different MLC models. In the rest of the examples the results are compared with ion chamber measurements, with the constant-width model and with film dosimetry.

Example 1: Application of Method 1 to Two Different MLC Models

In this example the $A(s)$ curves were obtained for two linear accelerators with different MLCs: a Varian high definition HD120 MLC (HDMLC) and a Varian Millennium 120 MLC. The asynchronous sweeping gap (aSG) tests were used with multiple gaps sizes (5 mm, 10 mm, 20 mm and 30 mm). For each gap size s values going from zero (no T&G) to a maximum s equal to the gap size (maximum T&G) were measured. Measurements were performed in water with a Farmer-type ion chamber.

Figure 7:
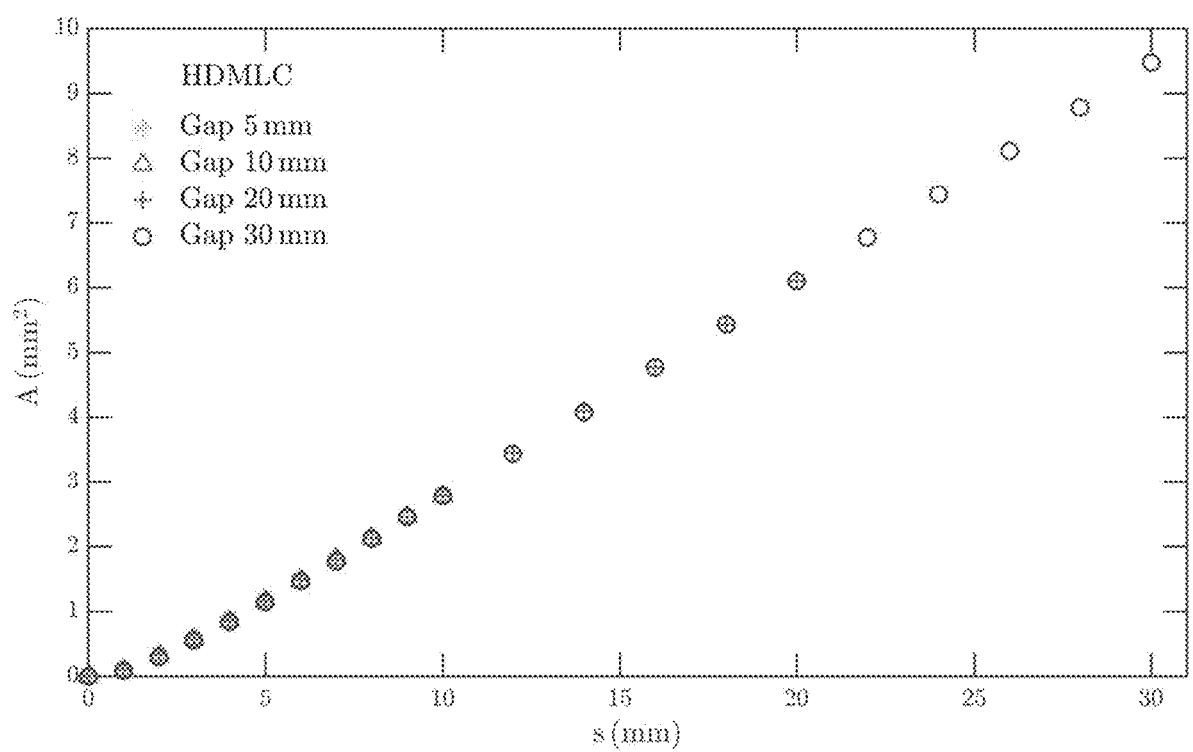
FIG. 7 illustrates the area to be subtracted, A(s), as a function of the shift s between adjacent leaf positions for a High Definition MLC (HDMLC). Data obtained with different MLC gap sizes is presented.
Figure 8:
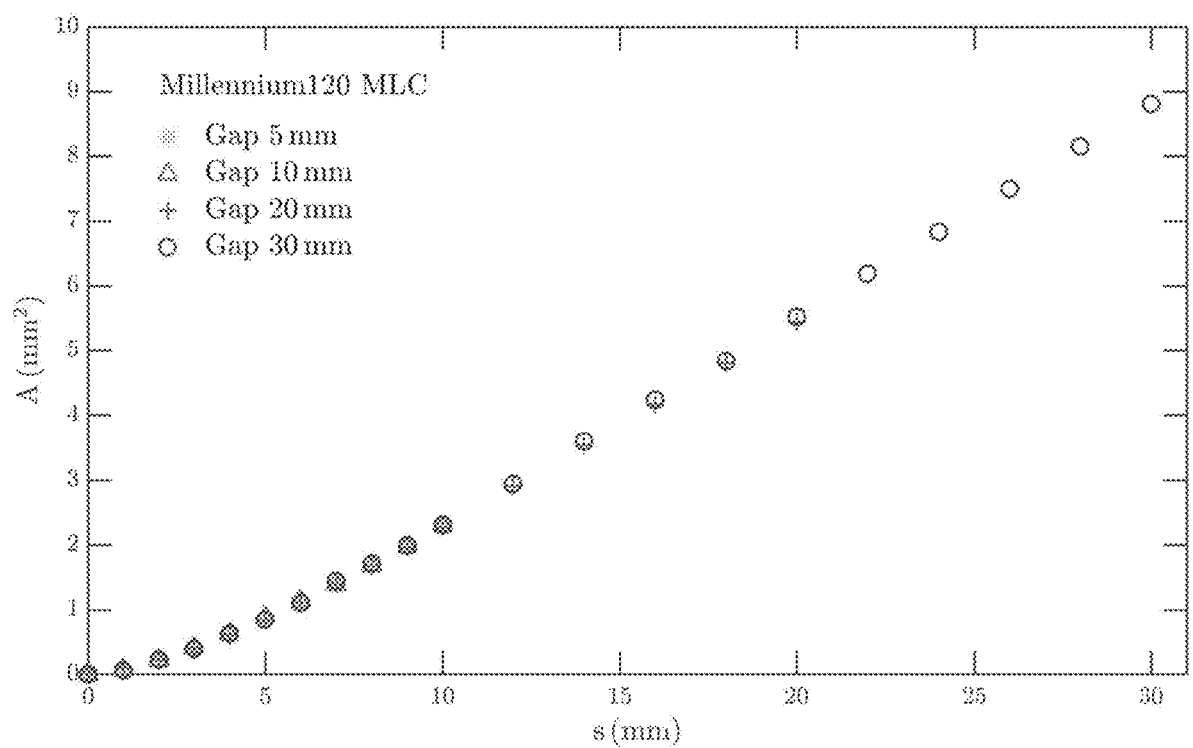
FIG. 8 illustrates the area to be subtracted, A(s), as a function of the shift s between adjacent leaf positions for a Millennium 120 MLC. Data obtained with different MLC gap sizes is presented.

The $A(s)$ values obtained for the various gap sizes and s values are illustrated in FIG. 7 (HDMLC) and FIG. 8 (Millennium 120). Consistent $A(s)$ values were obtained for the same s values using different gap sizes. This agreement validates the methodology used as well as the expressions previously derived and it shows that the $A(s)$ curve can be obtained and used regardless of the MLC gap size.

An analytic function was fitted to the experimental $A(s)$ curves. Since the curves were approximately linear for s>5 mm the following linear fit with an exponential correction was used:

$$A(s)=a_1 \cdot s - a_2 \cdot (1-e^{-a_3 \cdot s}). \qquad (32)$$

Eq. (32) can be reduced to two parameters by imposing that the TG profile $w(s)$ starts at zero because, taking into account Eq. (13)

$$w(o) = \frac{d(A(0))}{ds} = 0 \Rightarrow a_3 = \frac{a_1}{a_2}, \qquad (33)$$

and, therefore, $$A(s) = a_1 \cdot s - a_2 \cdot \left(1 - e^{-\frac{a_1}{a_2}s}\right). \qquad (34)$$

Figure 9:
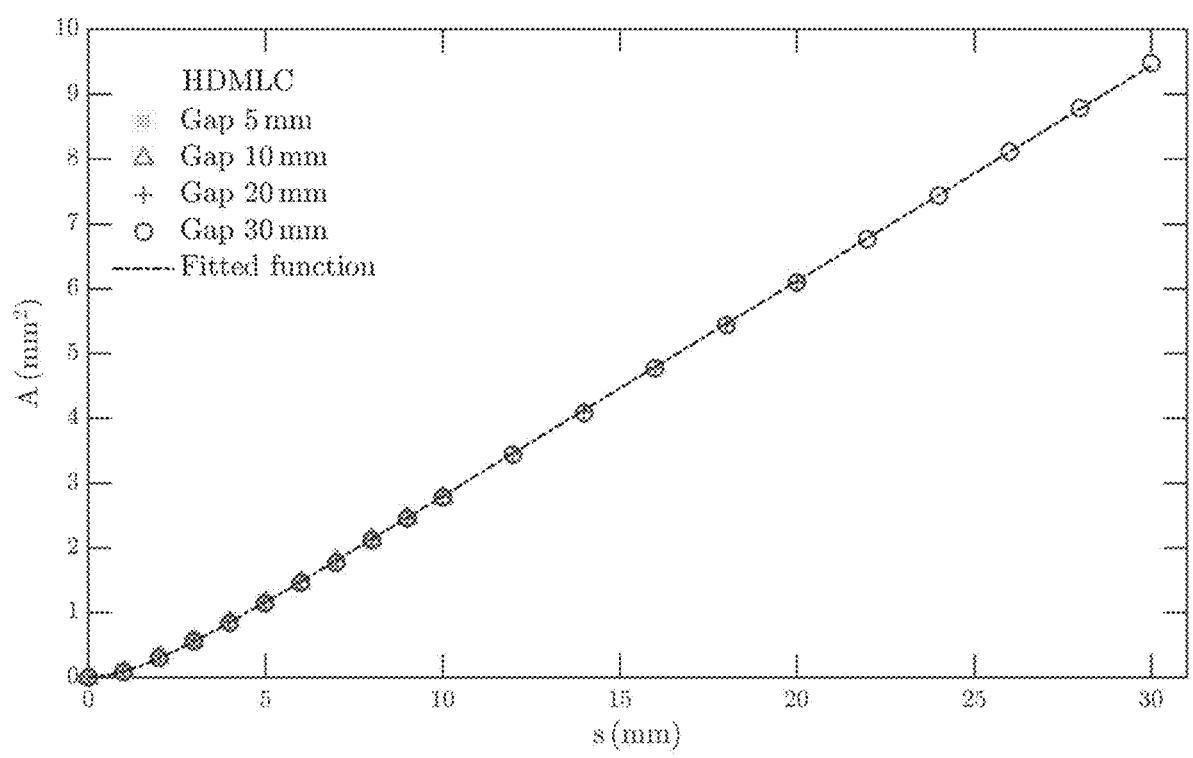
FIG. 9 illustrates a curve fitting the area to be subtracted, A(s), as a function of the shift s between adjacent leaf positions for a High Definition MLC (HDMLC). Symbols represent the experimental data for different MLC gap sizes.
Figure 10:
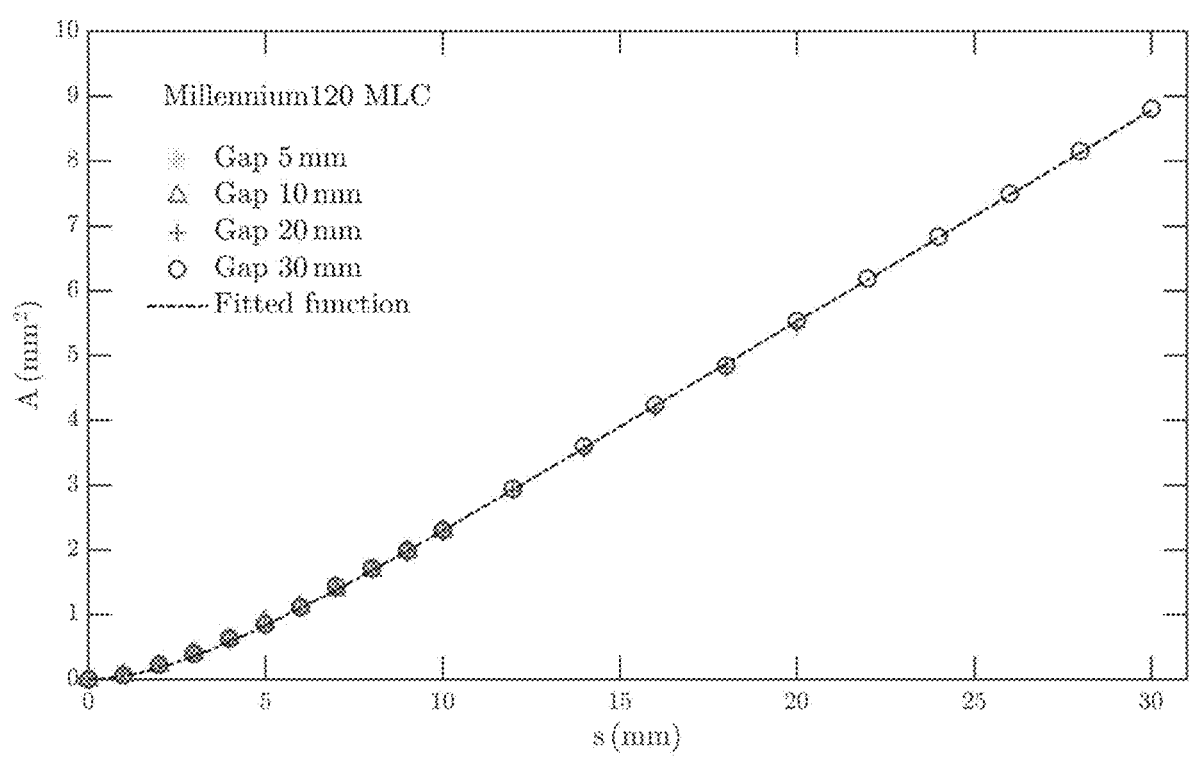
FIG. 10 illustrates a curve fitting the area to be subtracted, A(s), as a function of the shift s between adjacent leaf positions for a Millennium 120 MLC. Symbols represent the experimental data for different MLC gap sizes.

The curves fitted to the experimental $A(s)$ curves with Eq. (32) are illustrated in FIG. 9 (HDMLC) and FIG. 10 (Millennium 120). As it can be seen, they provide good estimates for the experimental $A(s)$ values, with differences with respect to the average experimental $A(s)$ values smaller than 0.1 mm². This shows that a simple equation with only two parameters can be used to fully describe the $A(s)$ curves.

Eq. (30) and Eq. (31) obtained with method 2 can also be used to fit the $A(s)$ curve, considering $w_{TG}$, μ and R as parameters or fixing R=160 mm and considering $w_{TG}$ and μ as parameters.

A difference between the $A(s)$ curves corresponding to the Millennium 120 MLC and the HDMLC models was found. Hence, different $A(s)$ curves were obtained for each MLC model and are presented in FIG. 11. The fitting parameters were $a_1$=0.332 mm, $a_2$=0.487 mm² for the HDMLC and $a_1$=0.326 mm, $a_2$=1.006 mm² for the Millennium 120 MLC.

Figure 11:
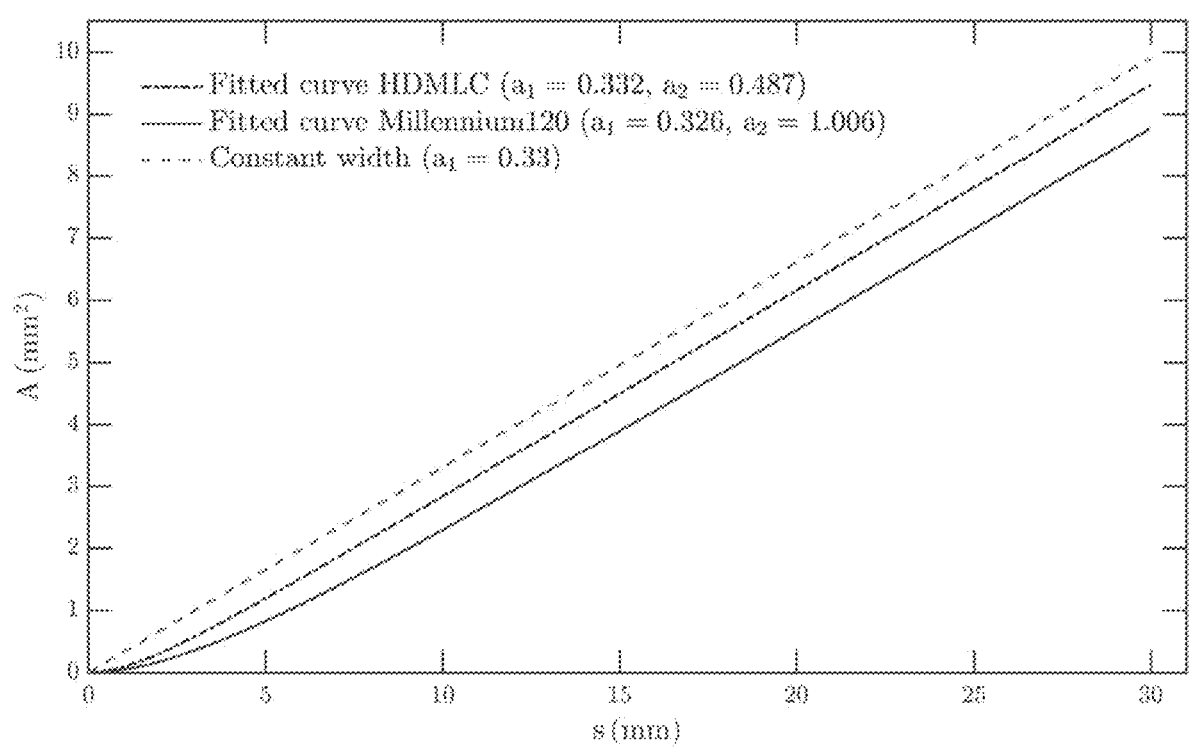
FIG. 11 shows the curves fitting to A(s) for two MLC models. A(s) corresponding to the constant-width model is also presented for comparison purposes.

The model subtracting a constant width from the fluence map to account for the TG effect is equivalent to considering a linear $A(s)$ curve with a constant slope. For comparison purposes this curve is also shown in FIG. 11 for a constant width of 0.33 mm.

The width $w(s)$ can be obtained with Eq. (13) as the first derivative of the $A(s)$ curve. Thus, considering the analytical expression used to fit the $A(s)$ curves given by Eq. (34), the optimal width (to be subtracted from the fluence map) results into:

$$w(s) = a_1\left(1 - e^{-\frac{a_1}{a_2}s}\right). \qquad (35)$$

Figure 12:
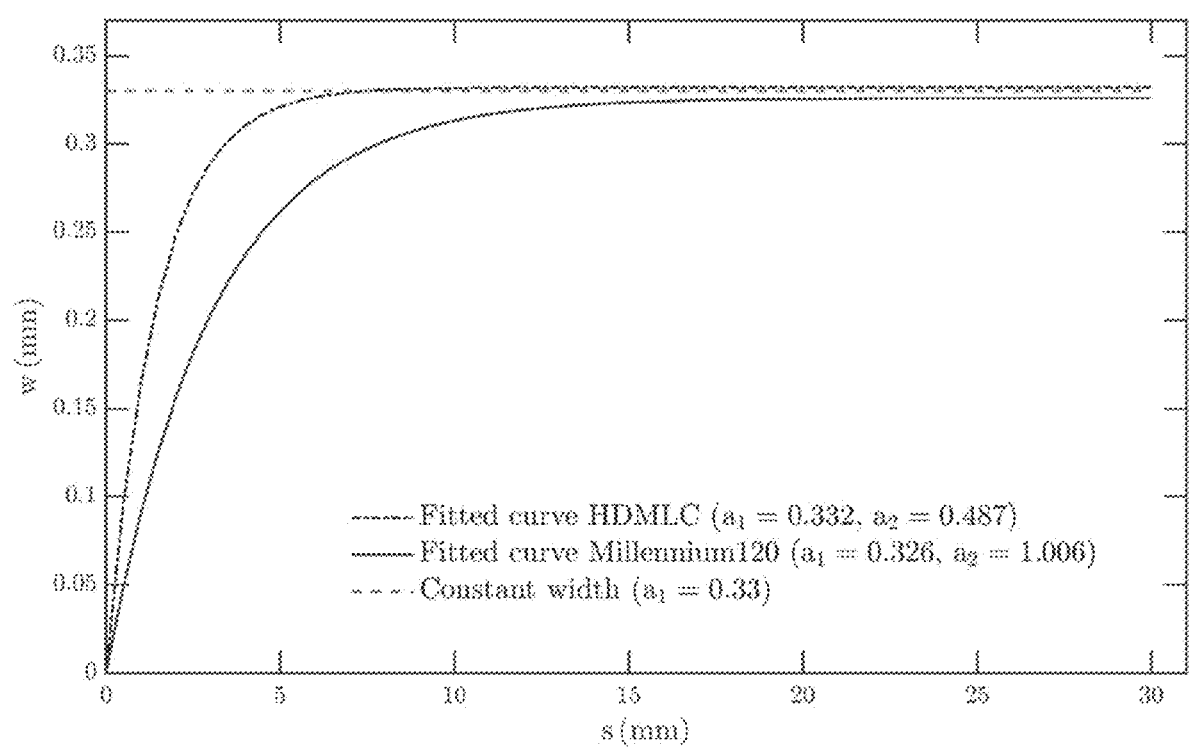
FIG. 12 shows the shapes of the width w(s) for two MLC models. A shape corresponding to the constant-width model is also presented for comparison purposes.

The shapes of the optimal width $w(s)$ obtained with Eq. (22) for each MLC are illustrated in FIG. 12. Again, the shape of the $w(s)$ for the model with a constant-width of 0.33 mm is also illustrated for comparison purposes.

As it can be seen, the shapes of the TG profiles deduced with the new model clearly differ from the constant tongue width. Indeed, the profile considered by the constant-width model clearly overestimates the TG width near the leaf tip (i.e., for small s values), therefore underestimating the fluence in that region and the corresponding calculated dose.

The fluence can be computed with Eq. (18) as:

$$\varphi = 1 - \frac{1}{p}\frac{d(A(s))}{ds} = 1 - \frac{w(s)}{p} = 1 - \frac{a_1}{p}\left(1 - e^{-\frac{a_1}{a_2}s}\right) \quad (36)$$

Thus, the empirical expression given in Eq. (34) to fit the experimental A(s) curve yields a fluence below the TG width that decays exponentially with s (i.e., with the distance to the leaf tip end). Other dependencies can be found depending on the analytical expression used to fit the experimental A(s) curve. For instance, if Eq. (30) and Eq. (31) (from method 2) are used to fit A(s) the fluence below the TG width will decay exponentially with $\sqrt{s}$, as in Eq. (28). Nevertheless, this fit produces practically the same results than those obtained with Eq. (36), with differences in average doses below 0.2% and differences in fluence profiles within a distance-to-agreement of 0.2 mm.

Example 2: Validation of the Model with Average Doses

In this example the fluence maps corresponding to aSG tests were obtained with Eq. (36) for the same MLC models used in Example 1. The dose distribution was then obtained by convolving the fluence maps with a Kernel and the average doses we computed.

Figure 13:
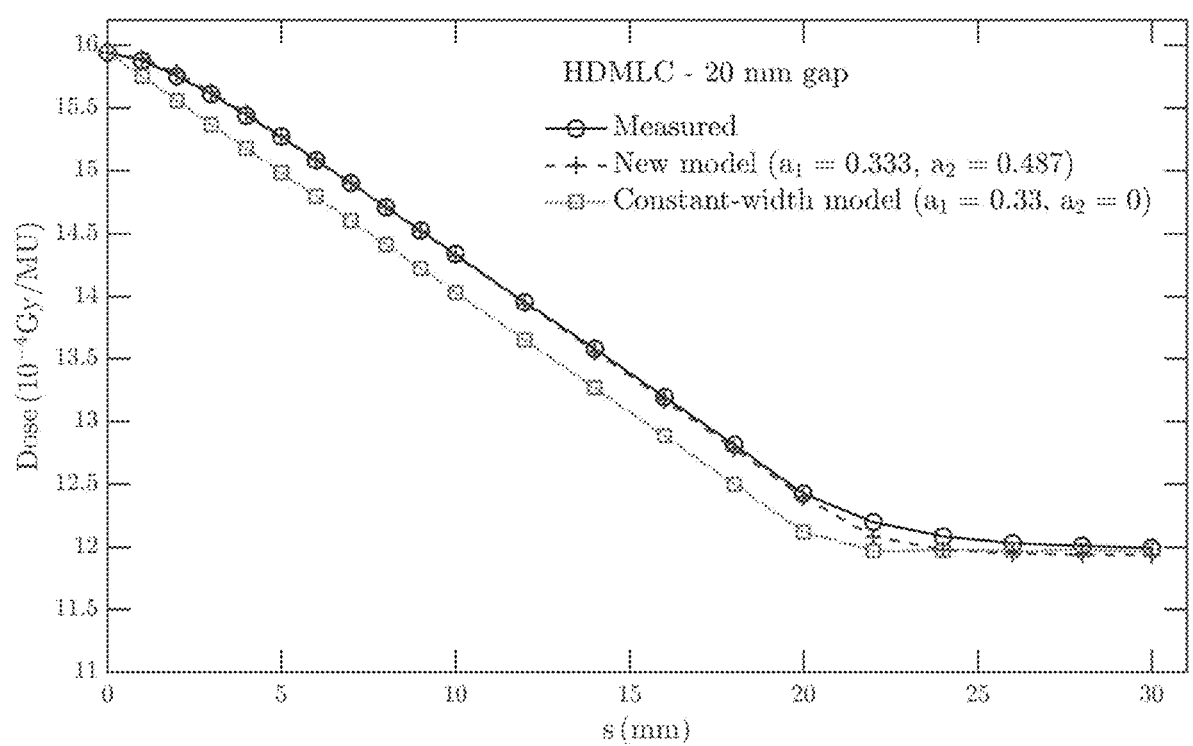
FIG. 13 illustrates measured and calculated average doses produced by asynchronous sweeping gap tests with different shifts s between adjacent leaf positions. The data corresponds to a gap size of 20 mm for the HDMLC model HD120.
Figure 14:
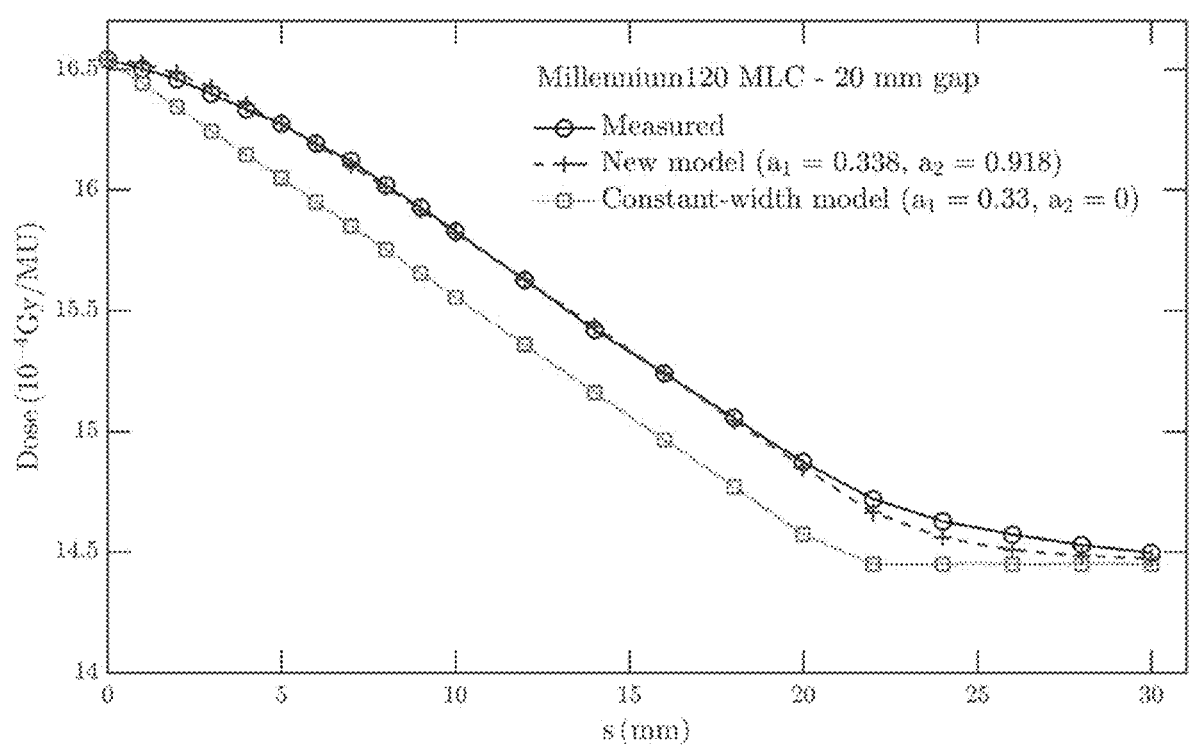
FIG. 14 illustrates measured and calculated average doses produced by asynchronous sweeping gap tests with different shifts s between adjacent leaf positions. The data corresponds to a gap size of 20 mm for the Millennium 120 MLC model.
Figure 15:
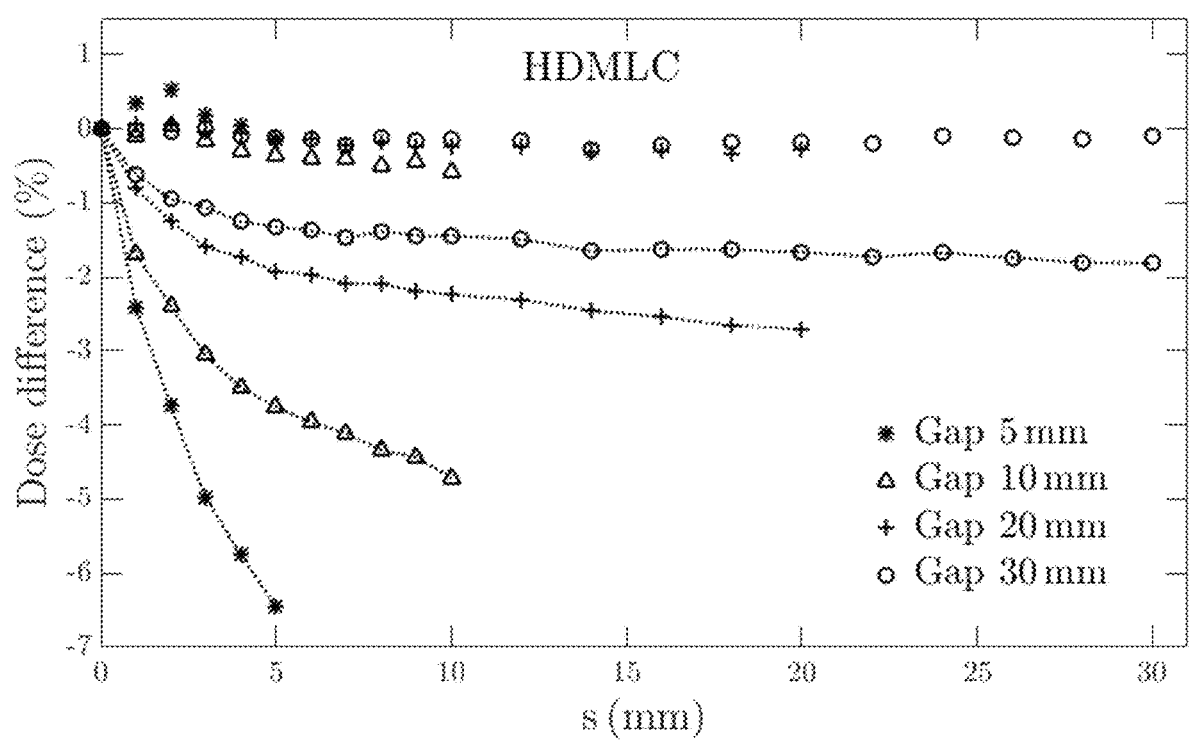
FIG. 15 shows the differences between measured and calculated average doses produced by asynchronous sweeping gaps with different shifts s between adjacent leaf positions. Data corresponds to different gap sizes and different accelerators with the HDMLC model (HD120). Symbols without lines indicate results with the new model and symbols with dashed lines indicate results with the constant-width model.
Figure 16:
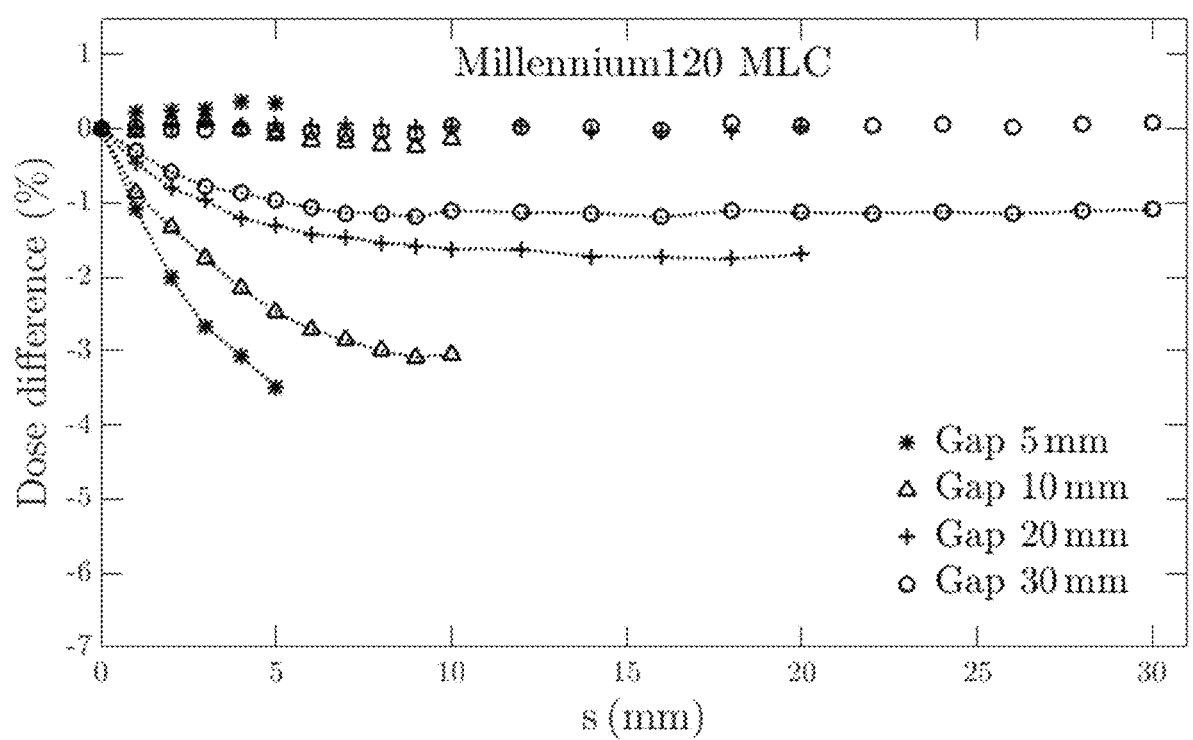
FIG. 16 shows the differences between measured and calculated average doses produced by asynchronous sweeping gaps with different shifts s between adjacent leaf positions. Data corresponds to different gap sizes and different accelerators with the Millennium 120 MLC model. Symbols without lines indicate results with the new model and symbols with dashed lines indicate results with the constant-width model.

Comparison between calculations and measurements for a representative gap size of 20 mm and different s values are given in FIG. 13 (HDMLC) and FIG. 14 (Millennium 120 MLC). Calculations with the constant-width model are also given for comparison purposes. Differences between calculations and measurements for different gap sizes and s values are provided in FIG. 15 (HDMLC) and FIG. 16 (Millennium 120 MLC). Symbols with dashed lines indicate differences with the constant-width model, while symbols without lines indicate differences with the proposed method (following Example 1).

As it can be seen, the proposed method produces results in very good agreement with measurements. All differences were within ±1%, even for the smallest gap size of 5 mm. On the contrary, the constant-width method produces much higher discrepancies, with differences of as much as 6% for the HDMLC. This is in agreement with the results found for these tests with commercial treatment planning system (Hernandez et al 2017).

Example 3: Improvement with Respect to the Constant-Width Model

In this example the results that can be obtained with the constant-width model are investigated taking into account an arbitrary value for the constant $w_{TG}$ parameter. To that aim calculations were performed for a collection of $w_{TG}$ values for s≤gap size and for each $w_{TG}$ the maximum difference in the average dose curves (FIG. 13 and FIG. 14) was recorded.

Figure 17:
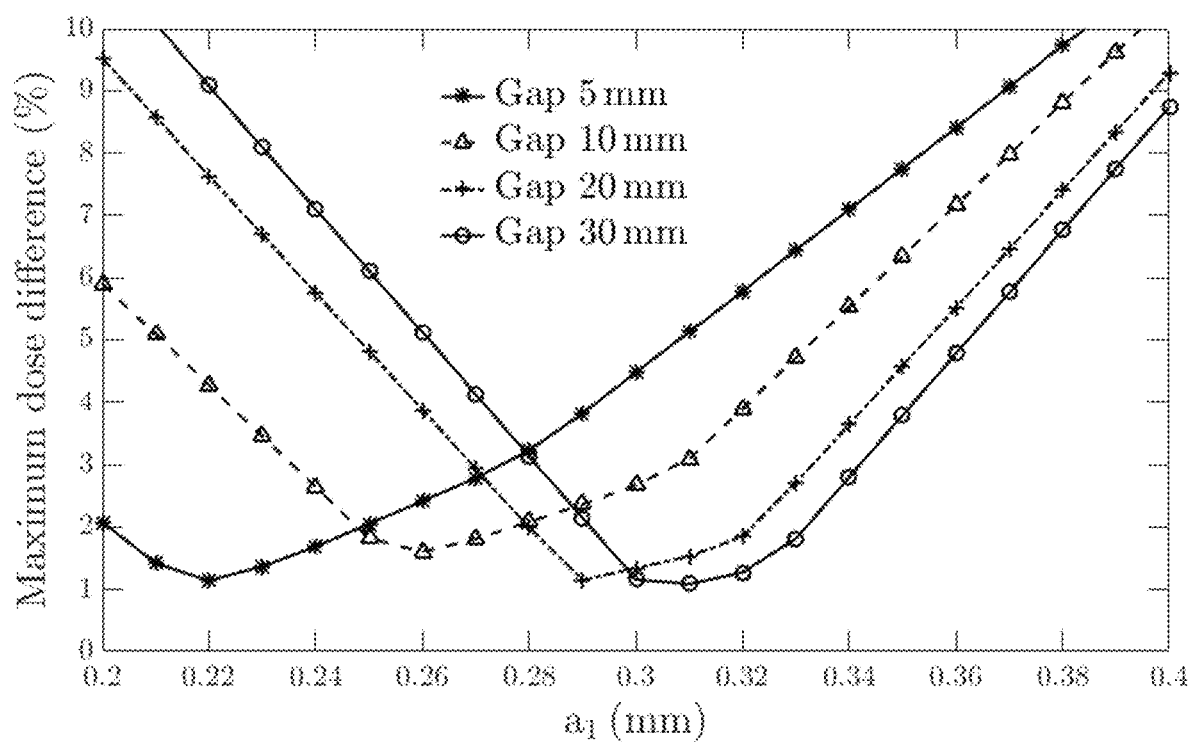
FIG. 17 provides the maximum differences between measurements of the asynchronous sweeping gaps and calculations with the constant width model ($a_2=0$) as a function of the TG width $a_1$. Data corresponds to different gap sizes with the HDMLC (HD120).

FIG. 17 shows the maximum differences obtained for each gap size as a function of the constant TG width. As it can be seen, a particular $a_1$ value can optimize the agreement for a certain gap size and reduce discrepancies to 1-2%, but no $a_1$ value can provide a good agreement for all gap sizes. Indeed, differences strongly depend on the gap size used and might be even greater if gap sizes larger than 30 mm were evaluated. On the other hand, as shown in Example 2, all differences obtained with the proposed model were within ±1%, which shows that the presented methods are more accurate than the constant-width model.

Example 4: Validation of the Model with Film Dosimetry

In this example a comparison of the calculations with the proposed model and film dosimetry is provided. Calculations were carried out using a resolution of 0.3125 mm and considering two values for the MLC transmission: interleaf transmission and intraleaf transmission.

Figure 18:
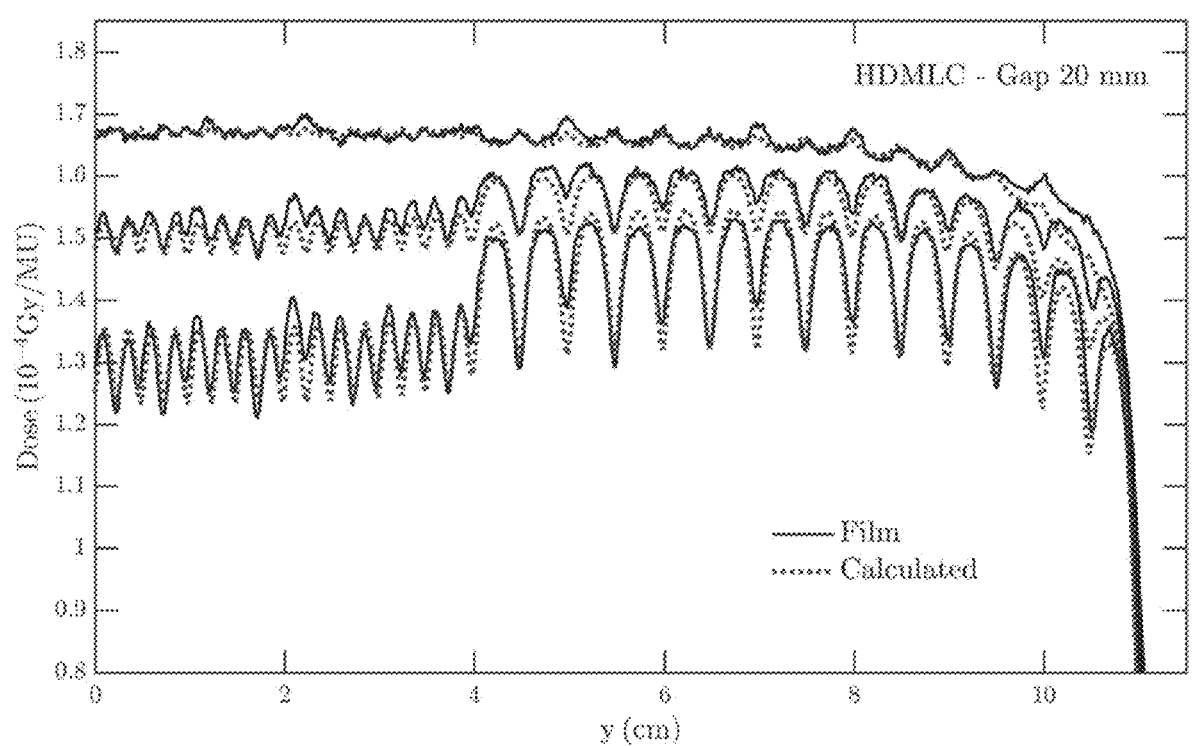
FIG. 18 illustrates the experimental and calculated profiles obtained for dynamic gaps of 20 mm. Results correspond to different TG fractions for the HDMLC MLC (HD120).
Figure 19:
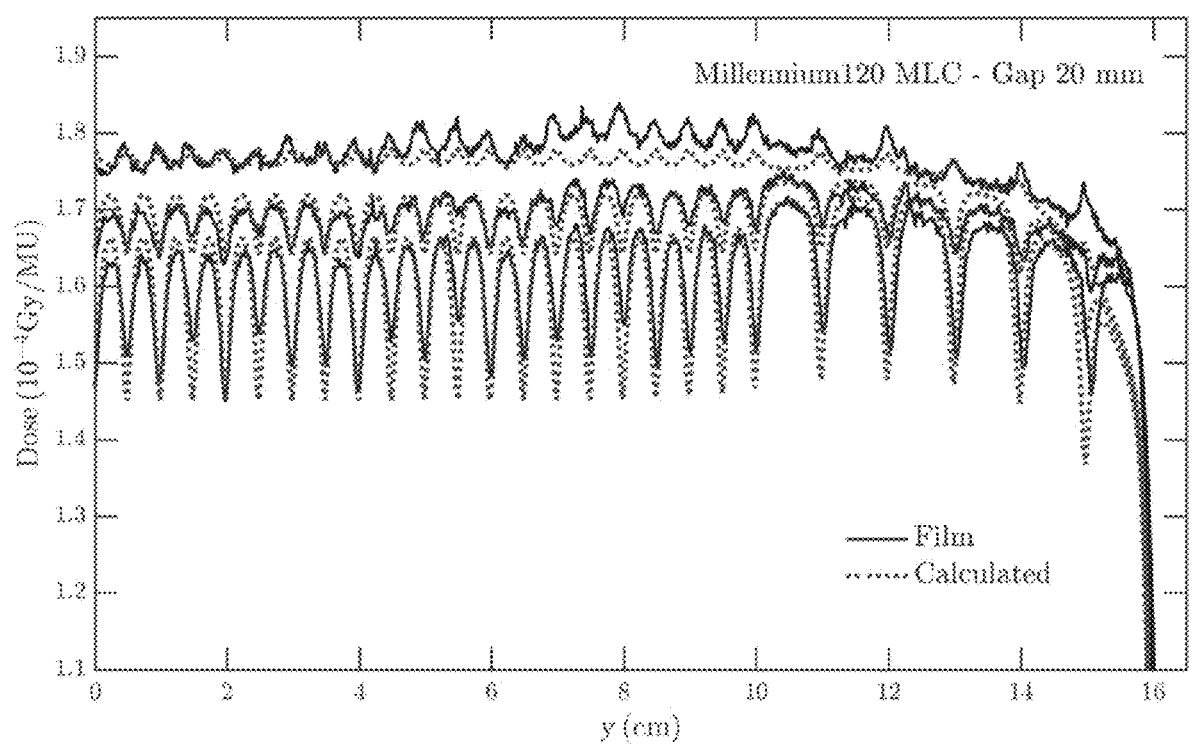
FIG. 19 illustrates the experimental and calculated profiles obtained for dynamic gaps of 20 mm. Results correspond to different TG fractions for the Millennium 120 MLC.

FIG. 18 and FIG. 19 show dose profiles in the Y direction (the direction perpendicular to the leaf motion) for sweeping gaps of 20 mm without TG (upper profile), with s=10 mm (mid profile) and for s=20 mm (lower profile). The calculated profiles accurately reproduce the fine details of the measured distribution, which proves that the proposed methods produce accurate calculations as long as interleaf transmission is considered and a sufficiently fine spatial resolution is used.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

The invention claimed is:

1. An improved method of calculating a radiation dose for a radiation treatment using a multi-leaf collimator for patients that will be treated with radiation therapy using the multi-leaf collimator comprising:
   providing a multi-leaf collimator comprising leaves of a tongue-and-groove design, the leaves having lateral edges and tip ends, wherein the lateral edges will be exposed to radiation during a treatment protocol,
   testing the multi-leaf collimator to determine a shape of a tongue-and-groove width, and
   subtracting the shape of the tongue-and-groove width from a fluence map used for radiation dose calculations,
   wherein an amount subtracted depends on a distance from a tip end of each leaf to a point on each leaf, and
   wherein the amount subtracted comprises a non-constant width at the lateral edges of the leaves that are exposed to radiation and a constant transmission through the non-constant width is considered.

2. The improved method of claim 1, wherein the testing comprises asynchronous sweeping gap tests with different shifts s between adjacent leaf positions.

3. The improved method of claim 1, wherein the testing comprises asynchronous oscillating sweeping gap (aOSG) tests with different shifts s between adjacent leaf positions.

4. The improved method of claim 1, further comprising calculating an area A(s) of a tongue-and-groove profile area between each tip end and a point on each leaf.

5. An improved method of calculating a radiation dose for a radiation treatment using a multi-leaf collimator for patients that will be treated with radiation therapy using the multi-leaf collimator comprising:
   providing a multi-leaf collimator comprising leaves of a tongue-and-groove design, the leaves having lateral edges and tip ends, wherein the lateral edges will be exposed to radiation during a treatment protocol, determining a shape of a tongue-and-groove width by testing the multi-leaf collimator, and subtracting the shape of the tongue-and-groove width from a fluence map used for radiation dose calculations, wherein an amount subtracted depends on a distance from a tip end of each leaf and a point on each leaf, and wherein the amount subtracted comprises a constant width at the lateral edges of the leaves that are exposed to radiation and a variable transmission through the constant width is considered.

6. The improved method of claim 5, further comprising obtaining the variable transmission with numerical methods taking into account a geometry of the leaves and a radiation transport across the multi-leaf collimator.

7. The improved method of claim 5, wherein the determining comprises testing the multi-leaf collimator by asynchronous sweeping gap tests with different shifts s between adjacent leaf positions.

8. The improved method of claim 5, wherein the determining comprises testing the multi-leaf collimator by asynchronous oscillating sweeping gap (aOSG) tests with different shifts s between adjacent leaf positions.

9. The improved method of claim 5, further comprising calculating an area A(s) of a tongue-and-groove profile area between each tip end and a point on each leaf.

* * * * *